United States Patent
Mewes et al.

(10) Patent No.: US 11,195,109 B2
(45) Date of Patent: Dec. 7, 2021

(54) MODELING AND PREDICTION OF BELOW-GROUND PERFORMANCE OF AGRICULTURAL BIOLOGICAL PRODUCTS IN PRECISION AGRICULTURE

(71) Applicant: DTN, LLC, Omaha, NE (US)

(72) Inventors: John J. Mewes, Mayville, ND (US); Robert C. Hale, Estes Park, CO (US)

(73) Assignee: DTN, LLC, Omaha, NE (US)

( * ) Notice: Subject to any disclaimer, the term of this patent is extended or adjusted under 35 U.S.C. 154(b) by 0 days.

(21) Appl. No.: 16/862,331

(22) Filed: Apr. 29, 2020

(65) Prior Publication Data
US 2020/0257997 A1 Aug. 13, 2020

Related U.S. Application Data

(63) Continuation-in-part of application No. 15/674,130, filed on Aug. 10, 2017, now abandoned.

(51) Int. Cl.
*G06N 5/04* (2006.01)
*G01S 19/14* (2010.01)
(Continued)

(52) U.S. Cl.
CPC ............. *G06N 5/04* (2013.01); *A01B 79/005* (2013.01); *A01C 21/007* (2013.01); *A01G 22/00* (2018.02);
(Continued)

(58) Field of Classification Search
CPC ...... G01N 33/0098; A01G 7/00; G06F 30/20; A01C 21/007
See application file for complete search history.

(56) References Cited

U.S. PATENT DOCUMENTS 5,668,719 A * 9/1997 Bobrov ............... A01C 21/007
702/2
6,999,877 B1 2/2006 Dyer et al.
(Continued)

FOREIGN PATENT DOCUMENTS

| WO | 2015051339 A1 | 4/2015 |
| WO | 2017053273 A1 | 3/2017 |

OTHER PUBLICATIONS

Jones, James W et al. "Brief history of agricultural systems modeling. "Agricultural systems vol. 155 (2017): 240-254. doi: 10.1016/j.agsy.2016.05.014 (Year: 2017).*
(Continued)

*Primary Examiner* — Akash Saxena
(74) *Attorney, Agent, or Firm* — Kutak Rock LLP; Brian L. Main (57) ABSTRACT

A below-ground agricultural biological performance modeling approach in precision agriculture combines customized field modeling with machine learning techniques for environmental matching of variables to describe a below-surface soil state, to understand and predict the performance of soil-active agricultural biological products such as biopesticides, bio-stimulants, plant growth regulators, and other biologically-derives soil adjuvants. The modeling approach characterizes the influence of environmental relationships on the performance of such soil-active agricultural biological products to develop a suite of predictive models to provide notifications, advisories, and recommendations for appropriate products for individual fields.

33 Claims, 2 Drawing Sheets

(51) Int. Cl.
  *G01N 33/24* (2006.01)
  *A01G 22/00* (2018.01)
  *G06N 20/00* (2019.01)
  *A01B 79/00* (2006.01)
  *G06F 30/13* (2020.01)
  *A01C 21/00* (2006.01)
  *G01S 19/42* (2010.01)

(52) U.S. Cl.
  CPC .............. *G01N 33/24* (2013.01); *G01S 19/14* (2013.01); *G06F 30/13* (2020.01); *G06N 20/00* (2019.01); *G01S 19/42* (2013.01)

(56) References Cited

U.S. PATENT DOCUMENTS

| | | | |
|---|---|---|---|
| 9,076,118 B1* | 7/2015 | Mewes | G06N 20/00 |
| 9,131,644 B2 | 9/2015 | Osborne | |
| 9,563,852 B1 | 2/2017 | Wiles et al. | |
| 9,743,574 B1* | 8/2017 | Maxton | A01C 21/007 |
| 10,362,726 B2 | 7/2019 | Zielke | |
| 11,068,625 B2* | 7/2021 | Gates | A01C 21/007 |
| 2002/0168417 A1 | 11/2002 | Blease et al. | |
| 2006/0015374 A1 | 1/2006 | Ochs et al. | |
| 2006/0196158 A1 | 9/2006 | Faivre et al. | |
| 2006/0200334 A1 | 9/2006 | Faivre et al. | |
| 2007/0208510 A1* | 9/2007 | Anderson | E02B 11/00 702/2 |
| 2007/0288167 A1* | 12/2007 | Anderson | A01B 79/005 702/2 |
| 2008/0140431 A1* | 6/2008 | Anderson | A01B 79/005 701/50 |
| 2014/0358486 A1* | 12/2014 | Osborne | G01N 33/0098 702/189 |
| 2015/0112595 A1* | 4/2015 | Brehmer | G06Q 50/02 702/3 |
| 2016/0180473 A1* | 6/2016 | Groeneveld | A01C 21/00 705/7.25 |
| 2016/0247079 A1* | 8/2016 | Mewes | G06N 5/048 |
| 2016/0363696 A1 | 12/2016 | Dao et al. | |
| 2017/0049044 A1 | 2/2017 | Stoller et al. | |
| 2017/0061052 A1 | 3/2017 | Gates et al. | |
| 2017/0090068 A1* | 3/2017 | Xiang | G06F 30/27 |
| 2018/0020622 A1* | 1/2018 | Richt | G06F 30/20 703/6 |
| 2018/0092295 A1* | 4/2018 | Sugumaran | A01C 21/007 |
| 2019/0050741 A1 | 2/2019 | Mewes et al. | |
| 2019/0050948 A1* | 2/2019 | Perry | A01C 21/00 |
| 2019/0230875 A1* | 8/2019 | Mewes | G06F 30/20 |
| 2020/0068797 A1* | 3/2020 | Folle | A01C 21/007 |
| 2020/0074023 A1* | 3/2020 | Nizami | G06F 30/20 |
| 2020/0184214 A1* | 6/2020 | Casas | A01C 21/007 |
| 2021/0010993 A1* | 1/2021 | Shibata | G06N 20/00 |
| 2021/0185887 A1* | 6/2021 | Ilbasi | A01C 21/007 |
| 2021/0224833 A1* | 7/2021 | Lei | G06Q 50/28 |

OTHER PUBLICATIONS

"Final Office Action Received for U.S. Appl. No. 15/674,130, dated May 15, 2018".

"Non-Final Office Action Received for U.S. Appl. No. 15/674,130, dated Oct. 18, 2017".

"Non-Final Office Action Received for U.S. Appl. No. 15/674,130, dated Oct. 29, 2019".

* cited by examiner

MODELING AND PREDICTION OF BELOW-GROUND PERFORMANCE OF AGRICULTURAL BIOLOGICAL PRODUCTS IN PRECISION AGRICULTURE

CROSS-REFERENCE TO RELATED APPLICATION(S)

This patent application claims priority to, and is a continuation-in-part of, U.S. non-provisional application Ser. No. 15/674,130, filed on Aug. 10, 2017, the contents of which are incorporated in their entirety herein. In accordance with 37 C.F.R. § 1.76, a claim of priority is included in an Application Data Sheet filed concurrently herewith.

FIELD OF THE INVENTION

The present invention relates to the field of precision agriculture. Specifically, the present invention relates to a system and method of assessing the impact of biological processes in a soil system, based on correlated relationships between environmental variables, to predict a future below-ground performance of soil-active agricultural biological products.

BACKGROUND OF THE INVENTION

Agricultural biologicals are products derived from or composed of living organisms that are used in agriculture to enhance plant productivity and fertility or to provide protection from pests and diseases. Such products inhibit or mitigate the effects of organisms or environmental conditions that have adverse consequences on crop growth, vigor, or yield, or that stimulate crop growth, vigor, or yield, either directly or through effects on an intermediary substance or organism. They include bio-pesticides such as fungi, bacteria and other organisms that help protect plants against insects, diseases and weeds. They also include plant bio-stimulants, which are biologically-derived substances or organisms that simulate natural processes to enhance nutrient efficiency, tolerance to abiotic stress, and crop quality. Other such products include plant growth regulators and other biologically-based soil adjuvants.

Existing approaches to identifying an appropriate agricultural biological product for use with crops, fields and soils typically involve replicating experiments with products at multiple locations to evaluate the consistency of performance and write environmental constraints for product label recommendations, if needed. Such field testing is a major component of the high cost and extensive time required to commercialize such biological agricultural products.

Predicting performance and writing recommendations for many agricultural biological products is more challenging and requires more extensive field testing compared to most agricultural chemical products due to greater environmental sensitivity. Identifying the relevance of different and temporally-variant environment factors is also complicated when the product itself is a living organism that is strongly influenced by environment, and activity is slower and efficacy is lower as compared to optimal environmental conditions. Recommendations for when, and if, to apply a product, and how to apply it, must therefore be matched more closely to the environment of the field than for other agricultural products.

Identifying the required environmental considerations for performance and writing locally adapted recommendations is particularly challenging for soil-active agricultural biological products such as bio-pesticides and bio-stimulants. Soil moisture and temperature influence the performance of these products both directly and indirectly through influence on the crop and soil microbiome. Direct effects include appropriate soil moisture for movement into the rhizosphere, and suitable moisture and temperature for survival and activity of microbial bio-pesticides and bio-stimulants. For systemically active biologicals, the rate of uptake of the biological by the crop's roots is influenced by soil moisture and temperature, thereby resulting in indirect effects of these environmental variables on product efficacy. Further, soil-active biologicals may interact with the microbiome naturally present within the soil, and can thus be used to increase populations of crop-beneficial microbiota or, conversely, reduce populations of microbes that are detrimental to crop yield or quality. The synergisms achieved between the applied biological and the naturally occurring microbiome are again dependent upon physical factors of the soil environment, including soil temperature and soil moisture. There is an additional technical challenge in evaluating such considerations, as characterizing the soil environment in an agricultural field is difficult, expensive and disruptive.

Evaluation of such considerations in the existing art is possible because the abundance of many pests, and the performance of many crops, correlate well with above-ground weather information. Nonetheless, predicting or understanding the performance of soil-active products such as bio-pesticides and bio-stimulants is limited by lack of understanding of below-surface conditions in existing modeling paradigms.

BRIEF SUMMARY OF THE INVENTION

The present invention provides systems and methods of characterizing the influence of environmental relationships on the performance of soil-active agricultural biological products, to develop a suite of diagnostic and predictive models to provide notifications, advisories, and recommendations for appropriate products for individual fields. These systems and methods link weather information, custom field modeling, and machine learning techniques to generate predictions for a future performance of a soil-active biological catalyst, such as bio-pesticides and bio-stimulants.

These systems and methods are provided in a below-ground agricultural biological product performance modeling framework that combines customized field modeling with machine learning techniques for environmental matching of variables to describe a below-ground environment, to understand and predict the performance of soil-active agricultural biological products. The present invention also provides a decision support tool that supports precision agricultural operations based on performance predictions for soil-active agricultural biological products, and enables users to customize the various modeling paradigms performed within the below-ground agricultural biological product performance modeling framework for specific outcomes.

When only above-ground weather data is available for environmental matching, soil moisture and temperature throughout the soil profile are latent variables. Any environmental matching therefore relies on a correlation of the soil moisture and temperature with above-ground weather observations, and that correlation must be consistent across time and space. Customized field modeling generates soil moisture and temperature at different depths in a soil system, and as with above-ground weather data, this can be summarized over time to construct the environmental variables for machine learning.

The application of machine learning approaches for environmental matching is useful for understanding or predicting the occurrence or abundance of organisms or their derivatives in agricultural fields, and the performance of crops or crop varieties at specific locations. Observations of organism occurrence or crop performance at a location are analyzed with environmental characteristics of those locations in order to understand or predict performance across a targeted agricultural landscape. Environmental characteristics may be measured at the location of observation, but GPS coordinates may also be recorded for the location of an observation and used to extract environmental characteristics from spatial databases of weather, soil and climate data.

The present invention may also utilize hierarchical and iterative training of machine learning algorithms to improve prediction for local conditions. Each agricultural biological product may be analyzed in a suite of predictive models that include a base model developed from geographically-dispersed multiple environment experiments and one or more locally adapted versions of the base predictive model developed by re-learning the base model with performance data for a smaller local region. Such a localized two-step approach using machine learning techniques enables the base model to capture general relationships between product performance and environment. A localized model adapts such a base model for the most predominant environmental influences in the local region, as well as how local management practices modify the influence of the environment on performance.

In addition to agricultural biological products, environmental matching through machine learning with variables generated by customized field models may also be advantageous for identifying agricultural pests that spend a significant portion of their life cycle in the soil. Outside of agriculture, the combination of customized field modeling and machine learning may also be used to predict and understand the performance of products for bioremediation of soils.

It is therefore one objective of the present invention to provide a system and method of evaluating and predicting a below-ground performance of a soil-active agricultural biological product in precision agriculture. It is another objective of the present invention to provide a system and method of examining an interaction of above-ground weather conditions and below-surface soil moisture and temperature at different depths to model a prediction of soil-active agricultural biological product performance. It is still another objective of the present invention to provide a system and method of developing customized field models to assess soil conditions at different depths and combining this knowledge with a measured efficacy of a soil-active agricultural biological product using machine learning techniques, to generate predictions of below-ground performance in a specific field.

It is yet another objective of the present invention to provide an advisory service with recommended management actions and other alerts and notifications to growers, landowners, crop advisors and other responsible entities regarding applications of agricultural biological products to crops, fields, and soils. It is still another objective of the present invention to provide a system and method of identifying agricultural pests that spend a significant portion of their life cycle in the soil using combined modeling approaches that examine the interaction of above-ground weather conditions and below-surface soil moisture and temperature at different depths. Yet another objective is to provide an indication to growers, landowners, crop advisors, and other responsible entities of product performance for bioremediation in soils and to enable one or more responsive management actions.

In one embodiment, a method comprises ingesting, as input data, above-ground weather data, represented by weather and climatological information that includes at least one of recent and current field-level weather data, historical field-level weather data and extended-range weather forecast data for a specific geographical area, crop-specific information relative to a crop in a particular field in the specific geographical area, soil-specific information relative to a soil system of the particular field, and a measured efficacy of a past performance of a soil-active agricultural biological product, wherein the soil-active agricultural biological product includes at least one of a bio-pesticide, a bio-stimulant, and a plant growth regulator. The method also includes modeling the input data in a plurality of data processing modules within a computing environment in which the plurality of data processing modules are executed in conjunction with at least one specifically-configured processor, the data processing modules configured to analyze a below-ground performance of the soil-active agricultural biological product, by applying the input data to characterize the influence of environmental factors on the soil-active agricultural biological product in a customized field model of one or more physical and empirical characteristics impacting the soil system, and configured to assess soil moisture and temperature by depth over time in the particular field, and correlating a significance of the above-ground weather data on the measured efficacy of the past performance of the soil-active agricultural biological product with the assessed soil moisture and temperature by depth in the particular field to develop an environmental profile for the soil-active agricultural biological product, by selecting one or more appropriate environmental predictors impacting biological processes in the particular field, by a) constructing variables describing a below-surface state of the soil system in the particular field to summarize the correlated significance of the above-ground weather data and the assessed soil moisture and temperature by depth over time, and b) matching the variables describing the below-surface state of the soil system in the particular field with the measured efficacy of the performance of the soil-active agricultural biological product, and generating, as output data, a prediction of the below-ground performance of the soil-active agricultural biological product from the environmental profile.

In another embodiment, a method of evaluating a below-ground performance of a soil-active agricultural biological product in precision agriculture comprises developing a customized field model of one or more physical and empirical characteristics impacting a soil system in a particular field, the customized field model configured to assess soil moisture and soil temperature by depth over time in the particular field and characterize environmental factors influencing performance of a soil-active agricultural biological product in the soil system of the particular field, based on crop-specific information relative to a crop in the particular field, soil-specific information relative to a soil system of the particular field, and a measured efficacy of a past performance of the soil-active agricultural biological product, wherein the soil-active agricultural biological product includes at least one of a bio-pesticide, a bio-stimulant, and a plant growth regulator, identifying one or more appropriate environmental predictors impacting biological processes in the particular field to develop an environmental profile for the soil-active agricultural biological product and to analyze a below-surface state of the soil system in one or more machine learning models configured to construct variables summarizing a correlated significance between above-ground weather data represented by weather and climatological information that includes at least one of recent and current field-level weather data, historical field-level weather data and extended-range weather forecast data for the specific geographical area, and the soil moisture and temperature by depth over time, and to match the variables summarizing a correlated significance with the measured efficacy of the performance of the soil-active agricultural biological product, and predicting a performance of soil-active agricultural biological product based on the environmental profile.

Still another embodiment is a system, in a computing environment including at least one computer-readable storage medium having program instructions stored therein and a computer processor operable to execute the program instructions to model a below-ground performance of a soil-active agricultural biological product within a plurality of data processing modules, the plurality of data processing modules including an initialization module configured to ingest above-ground weather data, represented by weather and climatological information that includes at least one of recent and current field-level weather data, historical field-level weather data and extended-range weather forecast data for a specific geographical area, crop-specific information relative to a crop in a particular field in the specific geographical area, soil-specific information relative to a soil system of the particular field, and a measured efficacy of a past performance of the soil-active agricultural biological product, wherein the soil-active agricultural biological product includes at least one of a bio-pesticide, a bio-stimulant, and a plant growth regulator, one or more modules configured to develop a customized field model of one or more physical and empirical characteristics impacting a soil system in a particular field, the customized field model configured to assess soil moisture and soil temperature by depth over time in the particular field and characterize environmental factors influencing performance of the soil-active agricultural biological product in the soil system of the particular field, and develop an environmental profile for the soil-active agricultural biological product by identifying one or more appropriate environmental predictors impacting biological processes in the particular field to analyze a below-surface state of the soil system in one or more machine learning models configured to construct variables summarizing a correlated significance of above-ground weather data for a specific geographical area including the particular field and the soil moisture and temperature by depth over time, and match the variables summarizing the correlated significance with the measured efficacy of the performance of the soil-active agricultural biological product, and a prediction module configured to generate a prediction of the below-ground performance of the soil-active agricultural biological product from the environmental profile.

Other objects, embodiments, features and advantages of the present invention will become apparent from the following description of the embodiments, taken together with the accompanying drawings, which illustrate, by way of example, the principles of the invention.

BRIEF DESCRIPTION OF THE SEVERAL VIEWS OF THE DRAWINGS

The accompanying drawings, which are incorporated in and constitute a part of this specification, illustrate several embodiments of the invention and together with the description, serve to explain the principles of the invention.

DETAILED DESCRIPTION OF THE INVENTION

In the following description of the present invention reference is made to the exemplary embodiments illustrating the principles of the present invention and how it is practiced. Other embodiments will be utilized to practice the present invention and structural and functional changes will be made thereto without departing from the scope of the present invention.

Figure 1:
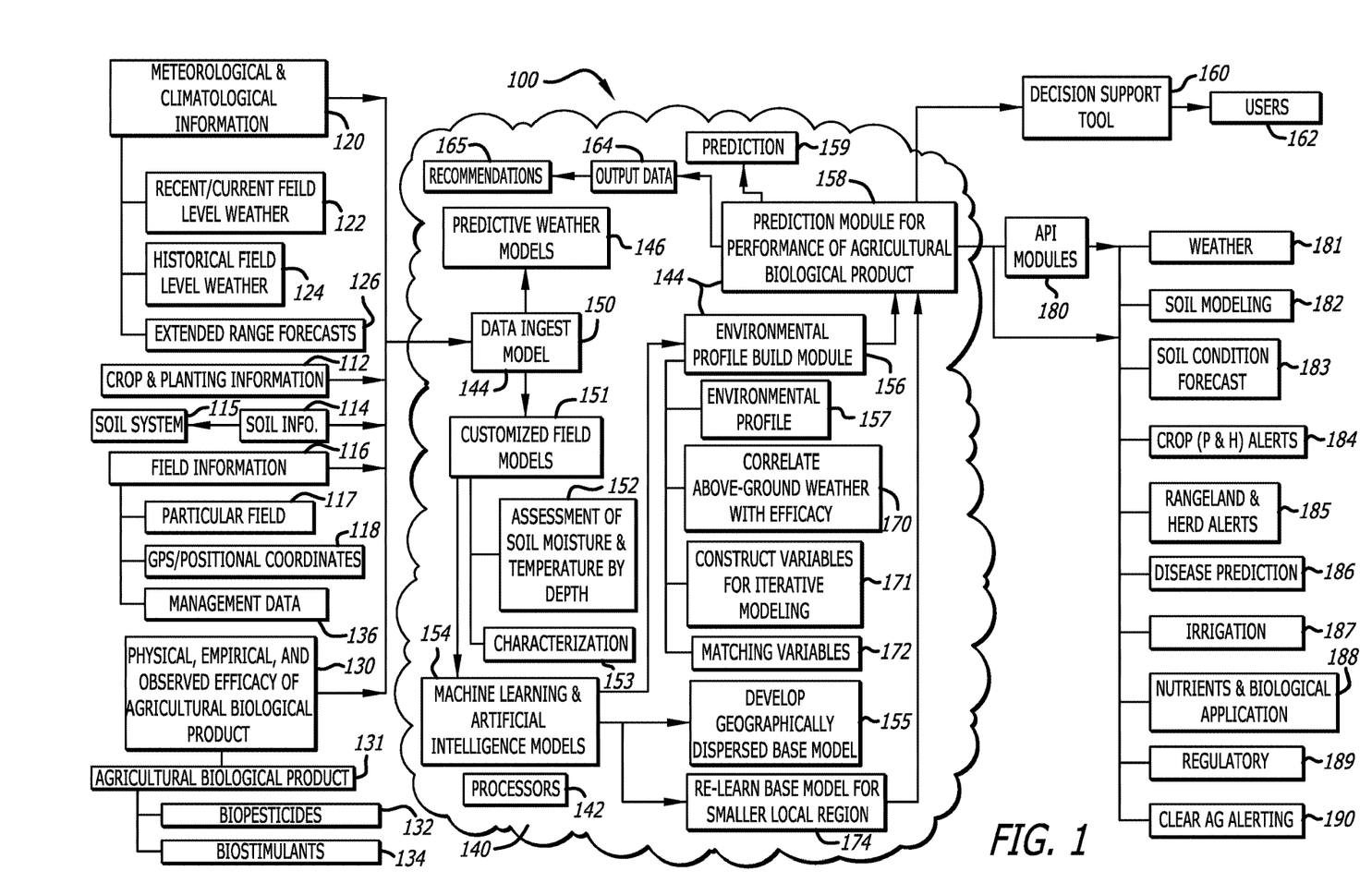
FIG. 1 is a block diagram illustrating components in a below-ground agricultural biological performance model according to one embodiment of the present invention.

The present invention is a below-ground agricultural biological performance model 100 for performing sub-surface assessments of a soil state, and for generating recommendations for agricultural activity from such assessments that impact the plant, crop, and soil ecosystem, as well as plant-soil biota interactions which lead to enhanced agricultural productivity. This below-ground agricultural biological performance model 100 presents multiple approaches for analyzing agricultural biological performance in precision agriculture, and is embodied in one or more systems and methods that at least in part include developing one or more customized field models, and one or more machine learning and artificial intelligence models, that together represent a suite of predictive models that analyze weather information, soil characteristics, and crop and field information, to characterize the influence of environment on the performance of soil-active agricultural biological products.

FIG. 1 is a systemic architecture diagram indicating various components and flow of information in the below-ground agricultural biological performance model 100. The model 100 is performed within one or more systems and/or methods that includes several components, each of which define distinct activities required to apply real-time, field-level data representative of crop, soil and field conditions in a particular field 117 and localized weather conditions, together with long-range climatological and/or meteorological forecasting, to customized field models 151 configured to assess soil moisture and temperature by depth 152 in the particular field 117. The present invention develops an environmental profile 157 for a particular soil-active agricultural biological product 131, to generate, in one embodiment, a prediction 159 of a below-ground performance of the particular soil-active agricultural biological product 131 and provide diagnostic support for management of agricultural operations related to the soil-active agricultural biological product 131. The prediction 159 of a below-ground performance of the particular soil-active agricultural biological product 131, as noted in further detail below, may be applied to produce information in many forms as output data 164, including but not limited to recommendations 166 for a product containing a specific agricultural biological, particular components of such a product, or a location in which the product containing a specific agricultural biological should or should not be used, according to various embodiments of the present invention. Other types of output data 164 include an advisory service 188 for crop/soil nutrient and other biological applications, which may be configured to develop, initiate, schedule, and perform targeted applications of soil-active agricultural biological products 131 as discussed further below for enhancing productivity in plant, crop and soil ecosystems, and improving plant-soil biota interactions, in a particular field 117.

The present invention permits improved evaluation of the below-ground performance of a soil-active agricultural biological product 131 in numerous ways. For example, soil temperature directly controls the rate of physiological activity of soil biota. While biological activity generally increases with increasing temperature, at least within specific temperature ranges, there are optimum organism-specific soil temperatures at which biological function performs best. Cellular processes may work less efficiently as soil temperatures deviate from this optimum, and cellular death may even occur in temperature extremes. While soil temperatures are often at least somewhat correlated with more readily-observable air temperatures, soil moisture, soil texture profiles, surface reflectance, residue cover, organic matter, and a host of other factors can all combine to create substantial variability in soil temperatures that cannot be discerned from atmospheric conditions alone. Use of a customized field model to simulate the interaction of ambient weather conditions with these various soil properties may lead to improved assessments of soil temperatures and their variability as a function of location and depth within the field over time, thereby enabling improved targeting of optimum timing and locations for a particular biological product.

Similarly, soil moisture may affect soil biota in at least two ways. Water is essential for the metabolic processes and associated enzyme activity of biologicals, and is a solvent for many biological nutrients. The degree to which soil pores are filled affects the viability, movement, reproduction, and predation of microorganisms in soil. Saturated soils and the corresponding anaerobic conditions may substantially slow or halt microbial processes that are dependent upon oxygen. However, soil moisture is even more difficult than soil temperature to estimate from the above-ground ambient weather conditions. The use of a customized field model again leverages weather data and the spatially-varying properties of the soil and plants within a field in order to produce a much more detailed and accurate picture of spatially- and temporally-varying soil moisture conditions within the field. In many cases, soil temperature or moisture conditions that are near-optimum for application of a particular biological product in one part of a field may coincide with highly-adverse conditions in another part of a field, based almost entirely on the variability of the more intransient soil properties across the field (such as the soil sand, silt, and clay fractions, the soil pH, soil organic matter, etc.). The movement of water through the soil profile is also important in terms of its impact as a transport mechanism for biologicals, either into or out of the optimum depth range for the particular product within the soil profile. A customized field model is able to make informed estimates of these vertical moisture fluxes by simulating the soil moisture distribution as a function of depth, relative to the holding capacities of the specific soils, and in light of both rainfall- and irrigation-based gains as well as evaporative and evapotranspirative losses.

Because of the complexity and variability of soil temperature- and moisture-related responses to ambient weather conditions, and the importance of accurate assessments of these conditions to the performance of certain biologicals, modeling approaches that analyze the impact of above-ground weather on moisture and temperature conditions throughout a soil profile to properly predict outcomes with regard to soil-active agricultural biological products are highly beneficial to enhancing productivity in plant, crop and soil ecosystems, and improving plant-soil biota interactions. Such modeling approaches allow for optimization, both spatially and temporally, in targeted applications developed for such soil-active agricultural biological products 131.

Returning to FIG. 1, the present invention is performed as noted above by building customized field models 151 of one or more physical and empirical characteristics impacting a soil system 115 in a particular field 117 to assess soil moisture and temperature by depth 152. This assessment of soil moisture and temperature by depth 152 is used to describe the below-surface soil state in an iterative process that constructs and matches variables to correlate above-ground weather information with efficacy 130 of a particular soil-active agricultural biological product 131. Together, these features comprise a complex modeling approach that enables predictions of a below-ground performance of the particular soil-active agricultural biological product 131 by building an environmental profile 157 representing the below-surface soil state to characterize the influence of environment on the performance of soil-active agricultural biological products.

The present invention is performed at least in part by applying a plurality of input data 110 to one or more data processing components 144 within a computing environment 140 that also includes one or more processors 142, a plurality of software and hardware components, and one or more modular software and hardware packages configured to perform specific processing functions. The one or more processors 142, plurality of software and hardware components, and one or more modular software and hardware packages are configured to execute program instructions or routines to perform algorithms for various functions of the below-ground agricultural biological performance model 100 described herein, and embodied in the one or more data processing components 144.

Input data 110 is ingested, received, requested, or otherwise obtained by a data ingest module 150, and includes meteorological and climatological information 120, crop and planting information 112, soil information 114, field information 116, and physical, empirical, and observation efficacy 130 of soil-active agricultural biological products 131. Each of these types of input data 110 includes different information relative to the environmental state, both above and below the surface ground, and influences performance of soil-active agricultural biological products.

Soil-active agricultural biological products 131 include any agricultural biologicals that have an impact on plant, crop and soil biomes. This may include both bio-pesticides 132 and bio-stimulants 134, as well as plant growth regulators and other biologically-based soil adjuvants, and any other biological-based product that may be applied to influence soil biota or performance of the plant, crop, and soil ecosystem. Examples of bio-pesticides 132 include biological fungicides and insecticides, and any fungi, bacteria and other organisms that help protect plants against insects, detrimental soil microbes, diseases and weeds. Examples of bio-stimulants 134 include biologically-derived substances or organisms that simulate natural processes to enhance nutrient efficiency and uptake, promote population increases of crop-beneficial soil microbes, increase, tolerance to abiotic stress and improve crop quality. Plant growth regulators are inoculants that either increase or reduce a rate of metabolic processes in a plant. Examples of plant growth regulators include bacterial soil inoculants that are applied to promote growth through the production of auxins, and *rhizobia* species that reduce localized levels of ethylene (a plant stress hormone) in the rhizosphere.

It is to be understood that the present invention is configured to model and predict the below-ground performance of many different kinds of soil-active agricultural biological products 131, and the present invention is not to be limited in scope to any one such agricultural biological product 131. It is to be further understood that the present invention may be configured to model and predict the below-ground performance of multiple soil-active agricultural biological products 131 at the same time, for example as to their performance relative to each other (where, for example, both a bio-pesticide and a bio-stimulant (or any other product combinations) are applied to a field 117 to address all of plant, crop and soil issues). It is to be further understood that soil-active biological products 131 may be used in conjunction with one or more chemical products introduced to the plant, crop, and soil biomes, either above ground, below ground, or both, and that the present invention may be configured to model and predict the performance of soil-active agricultural biological products 131 together with other chemical or synthetic additives. Developing targeted applications of soil-active agricultural biological products 131 may therefore include compiling information related to combined plant, crop and soil treatments that include both soil-active biological products 131 together with other products, regardless of whether they are biological, chemical, organic, synthetic, or any combination thereof, and initiating a combined application thereof.

The present invention contemplates that data 130 of soil-active agricultural biological products 131 may be applied relative to their efficacy in the particular field 117 or in any field having similar characteristics. Regardless, it is to be understood that the predictions 159 and output data 164 generated by the model 100 can be applied to any new fields, at any selected time, where efficacy has not yet been established.

It is to be additionally understood that the present invention is configured to model the below-ground environment for an understanding of both the crop and soil microbiome, and to predict performance of agricultural biological components that may be applied to influence the microbiome in an agricultural field 117. Therefore, the present invention is configured to model many aspects with respect to agricultural biological components, and may address both performance issues with respect to specific soil-active agricultural biological products 131, and also with respect to the wider condition on the agricultural microbiome generally.

Meteorological and climatological information 120 at least includes recent and/or current field-level weather data 122, historical field-level weather data 124, and extended-range forecasts 126, from many different sources as noted further herein. Recent and/or current field-level weather data 122 and historical field-level weather data 124 may represent in-situ or remotely-sensed or remotely-assessed observations for particular field or fields 117, and may also be derived from or provided directly via one or more crowd-sourced observations. The meteorological and climatological information 120 may be ingested into the present invention in raw, unprocessed form, or as processed data in the form of modeled, predicted or forecasted weather data over particular periods of time, such as short-range weather predictions and long-range, extended, and/or dynamical weather forecasts. This meteorological and climatological data 120 may be used to profile expected weather conditions for the particular field 117 to diagnose, predict and forecast expected weather conditions impacting soil conditions in a particular field 117, and/or in one or more geographical locations that may include the particular field 117. Alternatively, the meteorological and climatological information 120 may be applied to one or more weather models 146 to generate such a profile, and/or diagnose, predict, or forecast localized weather conditions.

Historical field-level weather data 124 may include information for at least one of a previous season(s), the period between a previous season(s) and the current season, and the current season. Current field-level weather data 122 for a particular field 117 may include both historical weather and short-term weather forecasts of field-level weather.

Meteorological and climatological data 120 may be collected from many different sources of weather information to provide one or more of the recent and current field-level weather data and short-term weather forecast data, for example as data that is complementary to the data assimilation systems and forecasting systems noted below. As noted above, weather information may be ingested into the present invention in either raw or processed form, from many different sources. Such sources of weather information may include data from both in-situ and remotely-sensed observation platforms. For example, numerical weather prediction models (NWP) and/or surface networks may be combined with data from weather radars and satellites to reconstruct the current and near-term forecasted weather conditions on any particular area to be analyzed. There are numerous industry NWP models available, and any such models may be used as sources of meteorological data in the present invention. Examples of NWP models at least include RUC (Rapid Update Cycle), WRF (Weather Research and Forecasting Model), GFS (Global Forecast System) (as noted above), and GEM (Global Environmental Model). Meteorological data is received in real-time, and may come from several different NWP sources, such as from the European Centre for Medium-Range Weather Forecasting (ECMWF), Meteorological Services of Canada's (MSC) Canadian Meteorological Centre (CMC), as well as the National Oceanic and Atmospheric Administration's (NOAA) Environmental Modeling Center (EMC), and many others. Additionally, internally or privately-generated "mesoscale" NWP models developed from data collected from real-time feeds to global and localized observation resources may also be utilized. Such mesoscale numerical weather prediction models may be specialized in forecasting weather with more local detail than the models operated at government centers, and therefore contain smaller-scale data collections than other NWP models used. These mesoscale models are very useful in characterizing how weather conditions may vary over small distances and over small increments of time. The present invention may be configured to ingest data from all types of NWP models, regardless of whether publicly, privately, or internally provided or developed.

Crop and planting information 112 may include data such as crop type, seed type, planting data, growing season data and projections, projected harvest date, crop canopy and soil conditions over time, relative maturity, planting or emergence date, crop temperature, crop moisture, seed moisture, plant depth, row width, and any other crop and plant information that may be used to develop the environmental profile 157 and the predictions of 159 forming the output data 164. Crop and planting information 112 may further comprise crop management information that incorporates all of the above types of data. Regardless, crop and planting information 112 may be provided as output data from one or more of phenology models of crop and plant growth, and other methods of predicting crop and plant growth over the course of a growing season, such as continual crop development profiling of the like disclosed in U.S. Pat. No. 9,131,644. Similarly, harvest data may be provided as output data from one or more models of harvestability, such as those disclosed in U.S. Pat. No. 9,076,118. Crop and planting information 112 may also provide further information about crop management actions for the particular field 117.

Soil information 114 may include many types of data representing state of a soil system 115, such as soil type, soil temperature, soil moisture content, soil porosity, soil pH, soil cation exchange coefficient, soil profile, soil organic matter, and mineral content, such as for example its sodicity. Soil information 114 may also include a temporal component, so as to represent conditions in a current growing season, or for a period of time extending until a following growing season, or for a prior growing season(s). Soil information 114 may be imported from one or more external database collections, such as for example the USDA NRCS Soil Survey Geographic (SSURGO) dataset containing background soil information as collected by the National Cooperative Soil Survey, or from one or more models configured to profile soil structure and composition. Soil information 114 may also be provided from growers or landowners themselves (or other responsible entities), from soil advisory tools, from farm equipment operating in a field, and any other source of such information.

Such other sources of information may include image data, such as remotely-sensed satellite imagery data and remotely-captured drone imagery data from orbiting satellites or remotely powered vehicles. When processed, such image data may provide details at a field-level resolution, which can be used by the predictive below-ground agricultural biological performance model 100 to improve both the environmental profile 157 and the predictions 159 generated within the present invention. It is to be noted that image data may also be incorporated to provide data pertaining to crop and planting information 112, field information 116, and management data 136, in addition to soil information 114.

Field information 116 includes data relative to at least a location of the particular field 117, and may include GPS data/or positional coordinates 118 that enables the below-ground agricultural biological performance model 100 to correlate input data 110 with respect to a particular field 117. Such GPS data 118 enables GPS receivers to determine positional coordinates and/or boundaries of a particular field 117, and allows the predictive below-ground biocatalyst performance model 100 to determine a geographical correlation at least for assessing soil moisture and temperature by depth 152 and building the environmental profile 157. Other methods of correlating input data 110 with a particular field or fields 117 may also be utilized and are within the scope of the present invention.

The positional coordinates of a particular field or fields 117 may also identify a specific agro-ecological zone for a more localized modeling of performance of soil-active agricultural biological products 131. While it is to be expected that weather patterns and crop, soil and field management practices are similar within a common agro-ecological zone, it should be noted that an agro-ecological zone may be defined by either or both environment and management practices, rather than merely using distance alone. Therefore, GPS/positional coordinates 118 may serve as variables in an environmental profile 157 depending, for example, upon how such an agro-ecological zone is defined.

Regardless of the type input data 110, information ingested into the present invention may also include image-based data, vehicular data, sensor data, and information from other third-party systems. Image-based data may be derived from systems such as video cameras, and vehicular data may be generated from one or more vehicle-based sensing systems, including those coupled to computing systems configured on farm equipment, or those systems configured to gather weather data from mobile devices present within vehicles, such as with mobile telephony devices and tablet computers. Sensor data may be provided from one or more sensors in or near a field, such as sensors configured on farm equipment or positioned throughout a field. Crowd-sourced observations may also be included in input data 110, and these may be provided from multiple sources, such as for example growers, farmers, land owners, equipment operators, crop advisors or consultants, and any other responsible entities. Crowd-sourced observations may be provided via oral or written reports, or electronically using mobile telephony devices or tablet computers, or any other computing devices that incorporate software tools such as mobile applications for accessing and using social media feeds.

In addition to the data ingest component 150, the plurality of data processing components 144 further include customized field models 151, machine learning and artificial intelligence models 154, an environmental profile build module 156, a base model for specific geographical regions 155, and a prediction and recommendation module 158. A further module may include one configured to perform predictive weather models 146 as noted above. Regardless, each of these are embodied in software and hardware components, and one or more modular software and hardware packages, configured to perform specific processing functions, modules, and modeling paradigms described herein.

At least some of these data processing components 140 are configured to generate output data 164 that may take many different forms. Output data 164 may include one or more recommendations 166 of agricultural activity, and based at least in part on the predictions 159, which may themselves constitute output data 164 generated by the prediction and recommendation module 158, and according to one or more embodiments of the present invention. These recommendations 166 may include those for appropriate agricultural biological products to be applied in the particular field 117, and more specifically may include, but are not limited to, recommendations 166 for a product containing a specific agricultural biological, particular components of such a product, or a time/location in which the product containing an agricultural biological should or should not be used. Output data 164 may also be provided to an agricultural decision support tool 160 that can be used to further predict performance of soil-active agricultural biological products 131, and for additional analytics and processing by one or more users 162.

Output data 164 (in the application advisory 188 or otherwise) may also include information, as noted above, that enables targeted applications of soil-active agricultural biological products 131 in plant, crop and soil ecosystems in a particular field 117. This may include, for example, information as to a type, amount and manner of soil-active agricultural biological product 131 to be applied, a time and place of such an application, as well as what other types of treatments may be applied in conjunction with the soil-active agricultural biological products 131, and carriers, agents or means for such a targeted application, whether as part of an application schedule, or as instructions or recommendations to develop, initiate perform, or schedule a targeted application, or both. Further information may include the amount, type, and manner of additives such as chemicals or non-organic treatments that are included with the application of the soil-active agricultural biological 131, and information providing reasons for such combinations. Still further information may also be included regarding specific details of the application itself, and it is to be understood that there are many examples of such further information. By way of further non-limiting examples, the output data 164 may include details such as the soil depth at which the application is to occur, a type of instrument to be used, a desired temperature of the particular soil-active agricultural biological product 131 itself, a desired post-application temperature of soil at varying depths and over time, a pressure at which the application is to occur, a time limit for the application, metadata that for example identifies a type of stimulant or pesticide applied and any non-organic or non-biological additives, labeling and regulatory compliance information, etc.

Many specific examples of targeted applications of soil-active agricultural biologicals 131 are contemplated and within the scope of the present invention. For example, the framework 100 may develop a targeted application of a soil-active agricultural biological 131 by generating an instruction for a scheduled application using a specific type of irrigation equipment, so that water is a carrier. This may include further information specifying a water pressure, a water amount, a specific ambient temperature, a specific water temperature, a specific duration, a specific window of a time, and a specific place in the particular field 117. In such an example, the targeted application of the soil-active agricultural biological 131 may be developed that specifies the use of a particular system configuration, such as surface irrigation, sub-surface irrigation, flood irrigation, drip irrigation, spray irrigation, or particular nozzles such as drop nozzles must be used, and may further specify other information such as whether the systems used are pivot or center-pivot systems, or systems that have been configured as linear move, lateral move, wheel-move, or side-roll irrigation systems. The framework 100 may further specify that an amount of water be applied with the soil-active agricultural biological 131 so that only the bare minimum amount of soil moisture is added at a particular depth to maintain a plant, root, or soil condition. Similarly, the targeted application may also specify or be limited to a particular irrigation timing or window of time during an application period. Information generated for such an exemplary targeted application may also include metadata, such as information relating to the delivery system type or mechanism and manufacturer characteristics, and associated resources and costs of delivery.

The output data 164 may include schedules of targeted applications of soil-active agricultural biologicals 131 within the instructions for initiating and performing such applications, and/or delivering a soil-active agricultural biological 131 according to the schedule. Schedules may include information related to a type, a timing, an amount, or any other characteristic of an application noted above. A schedule for a such a targeted application may be delivered to one or more of devices, equipment, third parties, or any other provider for enabling an immediate or future application of a soil-active agricultural biological 131. It is to be understood that a schedule for a targeted application may include substantive information related to the soil-active agricultural biological 131 itself, and any other characteristic that enables a delivery thereof.

The below-ground agricultural biological performance model 100 ingests all of this input data 110 and develops one or more agronomic models to produce the assessment of soil moisture and temperature by depth 152 and characterizations 153 of the influence of environmental factors on the performance of the soil-active biological product 131. These agronomic models are customized field models 151 that analyze one or more physical and empirical characteristics impacting above-ground plant canopy and below-surface soil conditions in a particular field 117. Such models 151 may include elements of crop, soil, plant, and other modeling paradigms, such as for example phenological models that include general crop-specific and crop variety-specific models, a common example being growing degree day (GDD) models. These models 151 may also include soil modeling elements such as the EPIC, APEX, and ICBM soil models, and land surface models such as the NOAH, Mosaic, and VIC models. Other models 151 contemplated within the scope of the present invention include crop-specific, site-specific, and attribute-specific physical models. It is contemplated that the input data 110 may be applied to existing precision agriculture models, as well as to customized models 151 developed for specific soil or field conditions.

The present invention develops such customized field models 151 to simulate agronomic problems and processes of interest to the agricultural community, because they are able to provide insight into the outcomes likely to be experienced by agricultural producers. When applied to models for diagnosing and predicting the soil conditions in a field, the prospects for providing improved guidance relating to agricultural operations are substantial. As noted above, land surface models are one prominent class of models for the simulation of soil conditions. Land surface models simulate the processes that take place at the interface between the surface of the Earth and its overlying atmosphere. Such simulations include, but are not limited to simulation of runoff and infiltration of precipitation off of or into the soil profile; drainage, vapor diffusion, capillary action, and root uptake of moisture within any number of layers within a soil profile; vertical diffusion and conduction of internal energy (heat) into, out of, and within the soil profile; plant growth and transpiration, including the impacts of weather and soil conditions on the properties and processes of this vegetation; and direct exchanges of moisture between the atmosphere and the soil (and plant) surfaces via evaporation, sublimation, condensation and deposition, among other processes. Elements of land surface modeling are useful in the present invention because they enable a correlation of above-ground weather observations with existing soil conditions, and development of environmental predictors through environmental matching of variables to describe below-surface soil conditions based on the assessment of soil moisture and temperature by depth 152 and the environmental profile 157.

Examples of commonly-used land surface models include the NOAH community land surface model, originally developed jointly by the National Centers for Environmental Prediction (NCEP), the Oregon State University (OSU), the United States Air Force, and the National Weather Service's Office of Hydrology (OH); the VIC model, or Variable Infiltration Capacity model, developed by the University of Washington's Land Surface Hydrology group; the Mosaic model, developed by the National Aeronautics and Space Administration (NASA); the Root Zone Water Quality Model (RZWQM), developed by the United States Department of Agriculture's (USDA) Agricultural Research Service (ARS); and the CLM model, or Community Land Model, a collaborative project between divisions and groups within the National Centers for Atmospheric Research (NCAR).

It is to be understood that there are many types of agronomic models available, and contemplated as within the scope of the present invention. Additionally, more than one modeling paradigm may be employed, and the customized field models 151 may apply elements of many models in combination with others. Therefore, the present invention is not to be limited by any one agronomic model referenced herein.

The assessment of soil moisture and temperature by depth 152 developed from the customized field models 151 is then applied to one or more layers of artificial intelligence models 154, trained to associate and compare the various types of input data 110 and identify relationships in such input data 110 to produce an environmental profile 157 which is ultimately used to generate output data 164. The customized field models 151, together with the layer of artificial intelligence models 154, enable the below-ground agricultural biological product performance model 100 to develop relationships between the various types of input data 110 to perform the correlations and matching in the environmental profile build module 156 that is used to formulate the environmental profile 157, which is used to predict performance of the agricultural biological product 131 in the particular field 117.

The present invention also contemplates that the relationships among the various types of input data 110 may be identified and developed in such a combined analysis by training the one or more layers of artificial intelligence 154 to continually analyze input data 110, to build a more comprehensive dataset that can be used to make far-reaching improvements to the customized field models 151 of physical and empirical characteristics for diagnosing and predicting the underlying soil condition. For instance, the one or more layers of artificial intelligence 154 can be applied to an adequately-sized dataset to draw automatic associations and identify relationships between the available external data and the soil condition, effectively yielding a customized model 151 for simulating below-surface soil properties in a particular field 117. As more and more data are accumulated, the information can be sub-sampled, the one or more layers of artificial intelligence 154 retrained, and the results tested against independent data in an effort to further customize agronomic models 151. Further, such modeling implicitly yields information as to the importance of related factors through weighting systems between inputs, subcomponents within the artificial intelligence layer(s) 154, and the output(s). This information may be used to identify which factors are particularly important or unimportant in the associated process, and thus help to target ways of improving the customized field models 151 over time.

The present invention contemplates that many different types of artificial intelligence may be employed within the scope thereof, and therefore, the one or more layers of artificial intelligence 154 may include one or more of such types of artificial intelligence. The one or more layers of artificial intelligence models 154 may apply techniques that include, but are not limited to, k-nearest neighbor (KNN), logistic regression, support vector machines or networks (SVM), and one or more neural networks. Regardless, the use of artificial intelligence in the below-ground agricultural biological performance model 100 of the present invention enhances the utility of physical and empirical agronomic models 151 by automatically and heuristically constructing appropriate relationships, mathematical or otherwise, relative to the complex interactions between soils and growing and maturing plants, the field environment in which they reside, the underlying processes and characteristics, and the efficacy data 130 made available. For example, where predictive factors known to be related to a particular outcome are known and measured along with the actual outcomes in real-world situations, artificial intelligence techniques are used to 'train' or construct a model 151 that relates the more readily-available predictors to the ultimate outcomes, without any specific a priori knowledge as to the form of those relationships.

The present invention therefore adopts a combined modeling approach for simulating the relationships between input data 110, predictive data and eventual outcomes, and may be thought of as performing one or more customized models 151 for assessing both a below-surface soil state and performance of soil-active agricultural biological products 131, and for generating the indicators and forecasts for agricultural activity comprising the output data 164 for a particular field 117. In the below-ground agricultural biological performance model 100, this approach permits the less well understood portions of the potential issues in the particular field 117 to be automatically modeled based on the relationships implicit in the particular input data 110 provided to the system. In additional embodiments, with sufficient input data and output reliability and accuracy, the customized field models 151 may be entirely supplanted by the use of artificial intelligence model(s) 154. Alternatively, the one or more layers of artificial intelligence 154 need not be employed in the system to produce the desired output data 164.

The assessment of soil moisture and temperature by depth 152 is used to develop the environmental profile 157 in the environmental profile build module 156. Together, the outcome of the customized field models 151 and the one or more layers of artificial intelligence 154 perform correlations 170 of the above-ground weather data and the efficacy data 130 for the agricultural biological product. Correlating a significance of the above-ground weather data on the measured efficacy 130 of the past performance of the soil-active agricultural biological product 131 with the assessed soil moisture and temperature by depth 152 in the particular field 117 is performed by selecting one or more appropriate environmental predictors impacting biological processes in the particular field 117, by constructing variables 171 describing a below-surface state of the soil system 115 in the particular field 117 to summarize the correlated significance of the above-ground weather data and the assessed soil moisture and temperature by depth 152 over time, for iterative modeling of the below-ground performance. The below-ground agricultural biological performance model 100 then performs a matching of variables 172, and provides this information to the prediction module 158 to produce the resulting assessment of performance of the agricultural biological product 131.

Efficacy 130 of an applied biological product, either in outcomes of one or more prior applications thereof, or in current applications thereof, is the effectiveness resulting from the application of a biological product on the plant, crop, or soil ecosystem. Efficacy 130 may be measured either directly or indirectly. Direct measurements of efficacy 130 may include, for example, population counts in terms of colony-forming units of the biological organisms applied or the targeted naturally-occurring microbes in the soil, total biomass of applied or targeted organisms, concentrations of specific biologically active substances, or the half-life of such substances under the particular environmental conditions during and after application of the biological product. Indirect measurements of efficacy 130 may include, for example, differences in crop performance or attributes under controlled experimental conditions where such performance or attributes from one or more fields to which the biological product has been applied are compared with one or more fields where the biological product has not been applied. Measurements of crop performance or attributes may include, for example, crop yield, crop biomass, root depth and distribution, or other measures of crop vigor. Below-ground performance of a soil-active agricultural biological product 131 applied in a targeted application thereof may be measured in similar ways, both directly and indirectly. Effectiveness of an applied biological product may be measured, for example, by in-situ observations of the performance of soil-active agricultural biologicals 131, or by further example, using one or more in-field or remote sensors, such as those configured or mounted on in-field agricultural equipment. It is contemplated that many methods of taking measurements of efficacy 130 may be utilized for analyzing effectiveness of the applied treatment, and are within the scope of the present invention.

Figure 2:
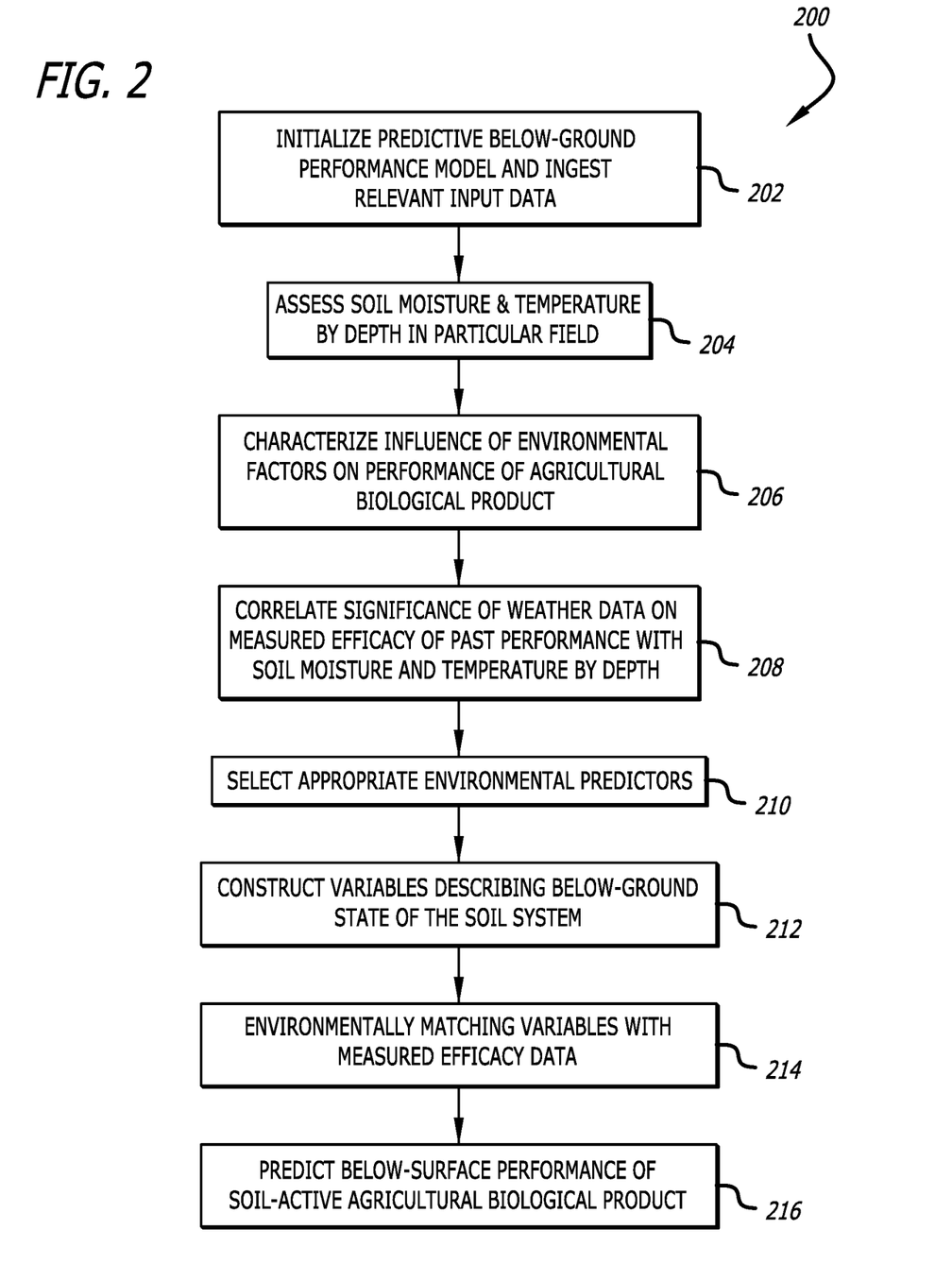
FIG. 2 is a flowchart of steps in a process of performing a below-ground agricultural biological performance model according to one embodiment of the present invention.

FIG. 2 is a flowchart of steps in a process 200 of performing the below-ground agricultural biological performance model 100 according to another embodiment of the present invention. In FIG. 2, the process 200 is initialized at step 202 by ingesting various types of input data 110, as noted above. The process 200 then applies this input data 110 to develop a customized field model 151 to perform an assessment 152 at step 204 of soil moisture and temperature by depth over time in the particular field 117, and to characterize 153 the influence of environmental factors on the performance of the soil-active agricultural biological product 131 at step 206.

The process 200 develops an environmental profile 157 of the soil-active agricultural biological product 131 by correlating at step 210 a significance of the above-ground weather data on the measured efficacy 130 of the past performance of the soil-active agricultural biological product 131 with the assessed soil moisture and temperature by depth 152. The process 200 further includes selecting, at step 212, one or more appropriate environmental predictors, by constructing variables 171 describing a below-surface state of the soil system 115 in the particular field 117 to summarize at step 214 the correlated significance of the above-ground weather data and the assessed soil moisture and temperature by depth over time 152, and by environmentally matching 172 the variables describing the below-surface state of the soil system 115 in the particular field 117 with the measured efficacy of the performance of the soil-active agricultural biological product 131 at step 216. At step 218, the process 200 then generates a prediction 159 of the below-ground performance of the soil-active agricultural biological product 131 from the environmental profile 157.

It is to be understood that the below-ground agricultural biological performance model 100 may be applied in different ways to arrive at specific outcomes. Therefore, output data 164 may take many forms, and the environmental profile 157 may be used in the present invention to develop specific information related to performance of agricultural biological products 131 in precision agriculture.

For example, the below-ground agricultural biological performance model 100 may be used to select particular mixture(s) or components for commercial products, in one embodiment of the present invention. Additionally, the below-ground agricultural biological performance model 100 may be applied to identify and recommend a specific product for a specific field 117, according to another embodiment of the present invention. The below-ground agricultural biological performance model 100 may also be applied to analyze performance with respect to a localized region for a single field recommendation for an individual field, or many potential fields in a regional analysis, according to yet another embodiment of the present invention.

In the embodiment where the below-ground agricultural biological performance model 100 is applied to identify and recommend a specific product for a specific field 117, the model 100 is developed by ingesting input data 110 comprised of field-specific information 116 such as geographic coordinates such as GPS & positional information 118 for the targeted field 117. This input data 110 is combined with other information, such as for example data relating to soil information 114 and meteorological and climatological information 120. This other information may be proprietary or acquired from third party sources, and may itself represent outcomes of models (proprietary or otherwise) for one or both of soil information 114 and meteorological and climatological information 120. Regardless, the model 100 may be developed to respond to a given weather scenario.

The present invention also contemplates that many different users and uses of this output data 164 are possible. Output data 164 from the below-ground agricultural biological performance model 100 of the present invention may be used to perform several functions, either directly or through other systems, hardware, software, devices, either using the agricultural decision support tool 160, or through one or more specific application programming interface (API) modules 180, or both.

Regardless of the use or user, the output data 164 may be tailored to provide specific management actions, whether it be in the form of a follow-on output from the tool 160, an advisory service, or an API 180. For example, the present invention may provide a weather advisory service 181 regarding a particular field or fields 117 that includes the meteorological and climatological information 120 and presents this information as a service for the particular field 117.

The present invention may also provide a soil modeling advisory 182 regarding a particular field or fields 117 that includes information regarding economic impact from using a specific agricultural biological product (or mix of products) in the particular field 117 at a specific time, and/or in a specific amount. Such a soil modeling advisory 182 may also include information that extends beyond the predictions 159 and recommendations 166 related to performance of a soil-active agricultural biological catalyst 131 described above. For example, the advisory service 182 may provide analytics of damage reflected in an environmental profile 157, such as for example an economic impact on a crop in the current growing season of particular soil conditions, or an economic impact from having to use certain field equipment or apply specific tillage practices to mitigate conditions discovered in various soil depths in the particular field 117. Other soil-related advisory services may include a soil conditions forecast service 183 based on information in the environmental profile 157.

Many additional agricultural advisories 180 are contemplated that relate to agricultural management practices. These may include a service 184 providing crop planting and harvest advisory alerts, a herd, feed, and rangeland management advisory service 185, a pest and disease prediction advisory service 186, an irrigation advisory service 187, and a crop/soil nutrient and other biological application advisory service 188.

The irrigation advisory service 187 may inform growers, landowners, or other responsible parties of irrigation mitigation actions, such as the positioning of flood, drip, and spray irrigation equipment, the timing of their use, and amounts of artificial precipitation to be applied. In still a further example, one or both of the herd, feed, and rangeland management advisory service 185 and the irrigation advisory service 187 may apply various types of data to provide information for irrigation requirements for achieving crop temperature and crop moisture thresholds for livestock herd management, in light of ground truth measurements and below-surface soil condition information in the environmental profile 157.

Additional management services may include a regulatory advisory service 189 for crops, soils, and groundwater or aquifers that is provided to owners of fields, growers of crops, and other responsible entities in relation to particular fields 117. Such a service may advise on possible contamination of soil beyond a specific acceptable range. For example, tillage of contaminated soils may easily spread airborne particles to other fields. Such an advisory 189 may therefore provide tillage practice analytics to manage contamination in the particular field 117 and beyond, such as models of the use of certain field equipment, and/or tillage timing and conduct. The regulatory advisory service 189 may combine the outputs of the customized field models 151 and the one or more layers of artificial intelligence 154 to produce an advisory based on the environmental profile 157. Such an advisory may indicate that a soil has a high contamination risk of a substance that requires federal or state reporting.

ClearAg and other alerting is still another service 190 contemplated by the present invention. ClearAg is an application offering a suite of precision agriculture services, and includes alerts that provide subscribers and other users with actionable information regarding harvest, planting, irrigation, pest/disease, nutrient, and other issues attendant to crop, field, and soil management.

The agricultural decision support tool 160 allows users to configure settings for below-ground agricultural biological performance model 100, using a display on a graphical user interface, and/or via web-based or application-based modules. Tools and pull-down menus on such a display (or in web-based or application-based modules) may also be provided to customize the input data 110, such as selecting different variables in the input data 110 as noted above.

The agricultural decision support tool 160 may be configured to customize the output data 164 for a specific use, or user, such as for example for a specific field, farm, crop, or piece of farm equipment, for a specific period of time. For example, the agricultural decision support tool 160 may be configured to generate an output signal, such as a numerical indicator comprising an indication to proceed with a specified action, to be communicated directly to a specified piece of farm equipment operating in the field. Many examples of such customized uses are possible. In another example, a signal to one or more pieces of irrigation equipment may be generated to proceed with, change a direction or angle of application of, or stop artificial precipitation from being applied to the particular field 117, or to a specific area of a particular field 117, in conjunction with an application of a specific biocatalyst or planned application of a specific biocatalyst. By way of further example, the agricultural decision support tool 160 may be configured to allow access to one or more automated processes for agricultural decision-making and recommendation-writing such as creating and defining management zones from the below-ground biocatalyst performance model 100. In addition to desktop, laptop, and mainframe computing systems, users may access the agricultural decision support tool 160 using applications resident on mobile telephony, tablet, or wearable computing devices.

Soil-active agricultural biologicals 131 are one of the fastest-growing agricultural inputs, and are an important segment within precision agriculture. Soil-active agricultural biologicals 131 comprise a diverse group of products, and are generally characterized as being derived from naturally-occurring microorganisms, plant extracts, beneficial insects, and other organic matter. They include any biological product which influences plant-soil biota interactions or the plant, crop, or soil ecosystem when introduced to soils, crops, plants, seeds, and any other component of such an ecosystem. A targeted application of a soil-active agricultural biological 131 may have different effects on soil biota and the plant, crop and soil ecosystem, depending on the type of product applied, the various conditions into which it is applied according to the customized land use model of the framework 100, as well as the method applied and mixture with other soil-active agricultural biologicals 131, chemicals, or other ingredients.

Soil-active agricultural biologicals 131 may comprise many different products, but are typically broken down into categories according to their use in agriculture. One such category is bio-stimulants. These are biological products that promote plant growth and productivity enhancement. Bio-stimulants are biologically-derived additives that are used in crop production to improve nutrient-use efficiency, assist plants in tolerating abiotic stresses like heat, cold, drought, and too much water, and improve quality attributes like nutritional content, appearance, and shelf-life.

Agricultural bio-stimulants may include bacterial or microbial inoculants, biochemical materials, amino acids, humic acids, fulvic acids, seaweed extracts, and other similar products, and may be used to supplement and enhance existing agricultural practices and crop inputs. Agricultural bio-stimulants are distinguishable from traditional crop inputs in that they operate through different mechanisms than fertilizers, regardless of the presence of nutrients in the products, and because they act only on the plant's vigor and do not have any direct actions against pests or disease. They are therefore complementary to crop nutrition and crop protection.

Agricultural bio-stimulants may further include compounds, substances and micro-organisms that are applied to plants or soils to improve crop vigor, yields, quality and tolerance of abiotic stresses. Bio-stimulants foster plant growth and development throughout the crop life cycle from seed germination to plant maturity in a number of demonstrated ways. These include improving the efficiency of the plant's metabolism to induce yield increases and enhanced crop quality, increasing plant tolerance to and recovery from abiotic stresses, facilitating nutrient assimilation, translocation and use, enhancing quality attributes of produce, including sugar content, color, fruit seeding, etc., rendering water use more efficient, enhancing soil fertility, particularly by fostering the development of complementary soil micro-organisms.

Another category of soil-active agricultural biologicals 131 are bio-pesticides. These are agricultural inputs that are typically used for plant protection or other bio-control mechanism. Bio-pesticides are derived from organic materials such as animals, plants, bacteria, and certain minerals. Bio-pesticides fall into three major sub-classes of natural pesticides: bio-chemical pesticides, microbial pesticides, and plant-produced materials, or Plant-Incorporated-Protectants (PIPs).

Bio-chemical pesticides are naturally-occurring substances for non-toxic control of pests. These substances interfere with, inactivate, or kill pests through non-toxic mechanisms that affect mating (by interfering, for example, with insect sex pheromones). They may also include scented plant extracts of many varieties which interfere with pest activity by, for example, attracting insects to traps.

Microbial bio-pesticides consist of a microorganism as the active ingredient, such as a bacterium, fungus, virus or protozoan. Microbial bio-pesticides are used to control many different kinds of pests. Each active ingredient may be relatively specific for targeting different kinds of pests. For example, some fungi control certain weeds, while other fungi kill specific insects. Microbial pesticides also include subspecies and strains of *Bacillus thuringiensis*, or Bt; each strain of this bacterium produces a different mix of proteins and specifically kills one (or a few) related species of insect larvae. The specific insect species to be affected is determined by whether the particular Bt produces a protein that can bind to a larval gut receptor, thereby causing the insect larvae to starve.

PIPs are a class of substances that plants produce from genetic material that has been added to the plant. For example, the gene for the Bt pesticidal protein may be introduced into the plant's own genetic material. This causes the plant itself, instead of the Bt bacterium, to manufacture the substance that destroys the pest.

Growers may use soil-active agricultural biologicals 131 for crop protection to complement chemical products in an integrated pest management (IPM) program, or as stand-alone treatments, for protecting plants from disease, insect pests and competition from weeds. Often, they are applied using the same equipment as for chemical products directly to plants or to the soil in which the plants are grown, or as a seed treatment. Because they may contain living organisms as active ingredients, bio-pesticides (and other soil-active agricultural biologicals 131) may have certain storage, handling and application requirements that are critical to their efficacy. Growers are responsible for management practices that adhere to these requirements, as well as thoroughly reading labels and following instructions from the manufacturer. Labels and instructions detail proper storage temperature, application timing and methods, product shelf life and compatibility.

Soil-active biologicals deliver lower levels of control and more variable performance than their chemical counterparts. For example, biologicals might reduce pest pressure, but not remove the pest entirely. Additionally, some biologicals take longer to act on the target disease or pest, but their effects may be longer lasting. Many biologicals are best used as a preventative and may perform the best when applied early in the season.

Still a further class of soil-active agricultural biologicals 131 are bio-fertility products. These products typically contain living cells of different of micro-organisms which have ability to convert nutritionally-important elements from unavailable to available form through biological processes. When applied for example to a soil, a seed, or a plant, the micro-organisms colonize the rhizosphere and promote growth by increasing the supply or availability of nutrients to the host system.

In performing assessments of soil moisture and temperature by depth 152, as well as building an environmental profile 157, comprehension of an active and healthy soil biota and its response to introduction of biological treatments is essential to improving and sustaining agricultural production in a particular field 117 for an eventual targeted application of soil-active agricultural biologicals 131. Soil biota comprise all living organisms in soil, from microorganisms to macrofauna, including roots. They are the active biological workhorse of soil, and include an incredibly diverse collection of organisms. An incredible and voluminous array of soil biota, including micro-organisms such as bacteria, fungi, and algae, as well as soil "animals" such as protozoa, nematodes, mites, springtails, spiders, insects, and earthworms, can live in an acre of soil and are more diverse than the community of plants and animals above ground. Soil biota are generally concentrated in plant litter, the upper few inches of soil, and along roots. Soil organisms interact with one another, with plant roots, and with their environment, to form the soil food ecosystem.

As soil organisms consume organic matter and each other, nutrients and energy are exchanged through the soil food ecosystem and are made available to plants. Each soil organism plays a role in the decomposition of plant residue, dead roots, and animal remains. Larger soil organisms, such as millipedes and earthworms, shred dead leaves and residue, mix them with the soil, and make organic material more accessible to immobile bacteria.

There are many physical factors which affect the activity of the soil biota, which consequently affect the type, amount, and timing of soil-active agricultural biologicals 131, and many other characteristics of their application in such a soil food ecosystem. These include temperature, pH, moisture, soil mineralogy, and light. Temperature directly affects the activity of the soil biota, by determining the rate of physiological processes such as enzyme activity and indirectly by affecting physio-chemical properties such as diffusion & solubility of nutrients, mineral weathering and evaporation rates and other aspects of such activity.

Within defined limits, biological activity increases with increasing temperature. Organisms have a specific range of temperature at which their biological activity operates. For common soil organisms the temperature range at which they can be active ranges from about 0° C. to about 60° C. This temperature range is largely determined by the temperature at which soil can reach although organisms may be able to survive outside the soils' temperature range or produce survival structures to allow them to survive under adverse conditions.

Within an organisms' temperature range, there is a temperature optimum at which biological function performs best. Beyond this value, cellular processes do not work as efficiently and as the temperature increases away from their upper limit there are irreversible changes to the cell properties, leading to cell damage or death. This means that generally those organisms which have a high temperature limit would tend not to be so active at the lower extreme compared to organisms more suited to the lower limit.

Organisms also have a range of pH within which they are active. Within certain limits, organisms can tolerate extremes, but this normally requires the cell to use additional energy in maintaining the correct internal cellular pH (pH 7.0). Some organisms, for example bacteria and archaea, can tolerate very extreme pH values such as pH 1 or pH 11 but these are extreme conditions are not normally found in agricultural soils. Larger soil animals may be more sensitive to pH than microorganisms. Earthworms, for example, are sensitive to low pH are not active in forest or peatland systems (pH <5), and their function is replaced by other organisms (enchytraeids in forests) or the soil forms in a different manner (peatlands).

Additionally, soil pH directly affects the solubility of elements. At an acidic pH, aluminum becomes more soluble and hence more available to the organisms with increased toxicity. Essential minerals can become unavailable at extremes of pH. For example, phosphorous and manganese become increasingly unavailable at high pH values.

Moisture content of soils affect the soil biota in at least two ways. Water is biologically essential for enzyme activity and metabolism, as well as for life generally, and is a solvent for biological nutrients and other chemicals. Physically, moisture content affects soil temperature (water is good conductor of heat) and soil aeration.

Additionally, the degree to which soil pores are filled affects the movement and predation of microorganisms in soil strata. In very dry soil, plants may not be able to extract enough water through their roots because of the energy it takes to remove water from small pores. This is known as the permanent wilting point, beyond which the plant cannot recover. Conversely, under wet conditions, oxygen does not diffuse through the soil as readily so the levels available to organism may become depleted, leading to anaerobic conditions. Fungi tend to be more resistant to water stress than bacteria, although under extreme conditions some bacteria can form resistant endospores which allow the organism to survive until more suitable conditions arise. Therefore, the type soil-active agricultural biological 131 to be introduced, and the intended impact on the soil biota, has a direct relation to moisture content.

Soil minerals are utilized by bacteria and fungi either as a direct source of energy for the soil biota or as a consequence of the production of acids such as sulphuric acid. Depending on the pH, some nutrients may become bound up with soil and become an unavailable, for example in clay soils. Clay soils have a number of sites on their surface which can bind enzymes and whole organisms, thereby affecting the movement of cells through soil and the breakdown of organic matter.

Light directly affects organisms on or just below the soil surface, and indirectly by heating the soil surface. Phototrophs, such as plants, algae and cyanobacteria, use the energy from sunlight to synthesis carbohydrates. In plants, some of this material finds its way into the soil biota via the roots, as well as from leaf fall. Some aspects of light are more damaging to organisms than others. For example, ultraviolet light may damage DNA and induce mutations in the organisms, which may result in death or biochemical degradation such as from changes of enzymes and metabolic pathways. This can produce structural changes within organic molecules, making them more, or less, easy to be degraded depending on the damage done.

The systems and methods of the present invention may be implemented in many different computing environments 140. For example, they may be implemented in conjunction with a special purpose computer, a programmed microprocessor or microcontroller and peripheral integrated circuit element(s), an ASIC or other integrated circuit, a digital signal processor, electronic or logic circuitry such as discrete element circuit, a programmable logic device or gate array such as a PLD, PLA, FPGA, PAL, and any comparable means. In general, any means of implementing the methodology illustrated herein can be used to implement the various aspects of the present invention. Exemplary hardware that can be used for the present invention includes computers, handheld devices, telephones (e.g., cellular, Internet enabled, digital, analog, hybrids, and others), and other such hardware. Some of these devices include processors (e.g., a single or multiple microprocessors), memory, nonvolatile storage, input devices, and output devices. Furthermore, alternative software implementations including, but not limited to, distributed processing, parallel processing, or virtual machine processing can also be configured to perform the methods described herein.

The systems and methods of the present invention may also be partially implemented in software that can be stored on a storage medium, executed on programmed general-purpose computer with the cooperation of a controller and memory, a special purpose computer, a microprocessor, or the like. In these instances, the systems and methods of this invention can be implemented as a program embedded on a mobile device or personal computer through such mediums as an applet, JAVA® or CGI script, as a resource residing on one or more servers or computer workstations, as a routine embedded in a dedicated measurement system, system component, or the like. The system can also be implemented by physically incorporating the system and/or method into a software and/or hardware system.

Additionally, the data processing functions disclosed herein may be performed by one or more program instructions stored in or executed by such memory, and further may be performed by one or more modules configured to carry out those program instructions. Modules are intended to refer to any known or later developed hardware, software, firmware, artificial intelligence, fuzzy logic, expert system or combination of hardware and software that is capable of performing the data processing functionality described herein.

The foregoing descriptions of embodiments of the present invention have been presented for the purposes of illustration and description. It is not intended to be exhaustive or to limit the invention to the precise forms disclosed. Accordingly, many alterations, modifications and variations are possible in light of the above teachings, may be made by those having ordinary skill in the art without departing from the spirit and scope of the invention. It is therefore intended that the scope of the invention be limited not by this detailed description. For example, notwithstanding the fact that the elements of a claim are set forth below in a certain combination, it must be expressly understood that the invention includes other combinations of fewer, more or different elements, which are disclosed in above even when not initially claimed in such combinations.

The words used in this specification to describe the invention and its various embodiments are to be understood not only in the sense of their commonly defined meanings, but to include by special definition in this specification structure, material or acts beyond the scope of the commonly defined meanings. Thus if an element can be understood in the context of this specification as including more than one meaning, then its use in a claim must be understood as being generic to all possible meanings supported by the specification and by the word itself.

The definitions of the words or elements of the following claims are, therefore, defined in this specification to include not only the combination of elements which are literally set forth, but all equivalent structure, material or acts for performing substantially the same function in substantially the same way to obtain substantially the same result. In this sense it is therefore contemplated that an equivalent substitution of two or more elements may be made for any one of the elements in the claims below or that a single element may be substituted for two or more elements in a claim. Although elements may be described above as acting in certain combinations and even initially claimed as such, it is to be expressly understood that one or more elements from a claimed combination can in some cases be excised from the combination and that the claimed combination may be directed to a sub-combination or variation of a sub-combination.

Insubstantial changes from the claimed subject matter as viewed by a person with ordinary skill in the art, now known or later devised, are expressly contemplated as being equivalently within the scope of the claims. Therefore, obvious substitutions now or later known to one with ordinary skill in the art are defined to be within the scope of the defined elements.

The claims are thus to be understood to include what is specifically illustrated and described above, what is conceptually equivalent, what can be obviously substituted and also what essentially incorporates the essential idea of the invention.

The invention claimed is:

1. A method, comprising:

ingesting, as input data, above-ground weather data, represented by weather and climatological information that includes at least one of recent and current field-level weather data, historical field-level weather data and extended-range weather forecast data for a specific geographical area, crop-specific information relative to a crop in a particular field in the specific geographical area, soil-specific information relative to a soil system of the particular field, and a measured efficacy of a soil-active agricultural biological product in an outcome of one or more prior applications of the soil-active agricultural biological product, wherein the soil-active agricultural biological product includes at least one of a bio-pesticide comprised of a biologically-derived pest control mechanism for plant, crop or soil protection, derived from organic materials such as one or more of animal matter, plant matter, bacteria, or minerals, a bio-stimulant comprised of one or more of compounds, substances and micro-organisms for promoting crop vigor, improving crop yields and quality, and tolerance of abiotic stresses, and a plant growth regulator comprised of plant or soil inoculants that either increase or reduce a rate of metabolic processes in a plant;

modeling the input data in a plurality of data processing modules within a computing environment in which the plurality of data processing modules are executed in conjunction with at least one specifically-configured processor, the data processing modules configured to analyze a below-ground performance of the soil-active agricultural biological product, by developing a customized field model of one or more physical and empirical characteristics impacting the below-ground performance of the soil-active agricultural biological product on soil biota of the soil system, to enable a targeted application schedule at a desired time and a desired place to obtain a specific outcome, by applying the input data to characterize the influence of environmental factors on the one or more prior applications of the soil-active agricultural biological product wherein the customized field model is configured to assess below-ground spatial and temporal attributes of importance to soil biota of the soil system that at least include soil moisture relative to a degree of soil pore saturation and temperature relative to a rate of physiological activity of soil biota at multiple depths and over multiple time periods, and correlating a significance of the above-ground weather data on the one or more prior applications of the soil-active agricultural biological product with the assessed below-ground spatial and temporal soil system attributes of soil biota of the soil system in the particular field to develop an environmental profile for the performance of the soil-active agricultural biological product on the soil biota at a below-surface state represented in the below-ground spatial and temporal soil system attributes, by selecting one or more appropriate environmental predictors impacting biological processes in the particular field, by a) constructing variables describing the below-surface state of the soil biota of the soil system in the particular field to summarize the correlated significance of the above-ground weather data and the assessed below-ground spatial and temporal soil system attributes of the soil biota, and b) matching the variables describing the below-surface state of the soil biota of the soil system with the outcome in one or more prior applications of the soil-active agricultural biological product;

generating, as output data, a prediction of the below-ground performance of the soil-active agricultural biological product on the soil biota from the environmental profile; and developing the targeted application schedule from the predicted below-ground performance for application of a specific soil-active agricultural biological product at a desired time or at a desired geographical location, wherein a user applies the specific soil-active agricultural biological product based on the targeted application schedule at the desired time or at the desired geographical location, or an automated application of the specific soil-active agricultural biological product at the desired time or at the desired geographical location is controlled based on the targeted application schedule.

2. The method of claim 1, further comprising applying the environmental profile to provide one or more advisories regarding an application of the soil-active agricultural biological product in any field at any selected time based on the prediction of the performance of the soil-active agricultural biological product.

3. The method of claim 1, wherein the input data further includes field-specific data that includes positional information identifying the particular field, the positional information including GPS data that enables usage of GPS receivers to determine one or more of positional coordinates and boundaries of the particular field.

4. The method of claim 1, wherein the input data further includes soil-water information for the particular field, the soil-water information including one or more of surface and sub-surface drainage characteristics, an amount of water applied to the soil system through effective rainfall and irrigation, an amount of water that is retained in a dynamically-growing root zone, an amount of water depleted from the dynamically-growing root zone, and irrigation-specific information relative to past, recent, or planned irrigation activity.

5. The method of claim 1, where the soil-specific information includes one or more of a soil type, and known soil temperature and moisture content for at least one of a current growing season and a period of time extending up to and including a current growing season.

6. The method of claim 1, wherein the crop-specific information further includes one or more of crop type data, planting data, crop growth data, growth stage-dependent parameters indicative of one or more crop growth stages, crop relative maturity data, crop planting depth and row spacing data, and targeted crop moisture or temperature thresholds.

7. The method of claim 1, wherein the input data further includes field-level remotely-sensed imagery data of the particular field.

8. The method of claim 1, wherein the correlating a significance of the above-ground weather data on the outcome of the one or more prior applications of the soil-active agricultural biological product with the assessed below-ground spatial and temporal attributes of soil biota of the soil system in the particular field further comprises iteratively selecting the one or more appropriate environmental predictors to develop one or more geographically-dispersed machine learning base models for a particular soil-active agricultural biological product, and applying the one or more geographically-dispersed machine learning base models to environmentally match the particular soil-active agricultural biological product for a particular geographic area.

9. The method of claim 8, further comprising training the one or more geographically-dispersed machine learning base models with performance data representing efficacy of the particular soil-active agricultural biological product for a smaller local region to re-learn the one or more geographically-dispersed machine learning base models for a specific localized geographical area within the smaller local region.

10. The method of claim 1, further comprising automatically developing an artificial intelligence model to analyze time-varying characteristics of the soil biota of the soil system, by building a comprehensive dataset for the customized field model of one or more physical and empirical characteristics impacting the soil biota of the soil system, and applying the artificial intelligence model to predict a below-ground performance of a soil-active agricultural biological product in any field at any selected time.

11. The method of claim 1, wherein the customized field model is further configured to determine an application of the soil-active agricultural biological product in conjunction with one or more of an additional biological product or a synthetic product in the particular field, and generate a prediction of the below-ground performance of the soil-active agricultural biological product and the one or more of an additional biological product or a synthetic product.

12. A method of evaluating a below-ground performance of a soil-active agricultural biological product in precision agriculture, comprising:
    developing a customized field model of one or more physical and empirical characteristics impacting below-ground performance of a soil-active agricultural biological product in on soil biota of a soil system in a particular field to enable a targeted application schedule at a desired time and a desired place to obtain a specific outcome, the customized field model configured to assess below-ground spatial and temporal attributes of importance to soil biota of the soil system that at least include soil moisture relative to a degree of soil pore saturation and soil temperature relative to a rate of physiological activity of soil biota by at multiple depths and over multiple time periods, and characterize environmental factors influencing performance of a soil-active agricultural biological product on the soil biota of the soil system of the particular field, based on crop-specific information relative to a crop in the particular field, soil-specific information relative to the soil system of the particular field, and a measured efficacy in an outcome of one or more prior applications of the soil-active agricultural biological product, wherein the soil-active agricultural biological product includes at least one of a bio-pesticide comprised of a biologically-derived pest control mechanism for plant, crop or soil protection, derived from organic materials such as one or more of animal matter, plant matter, bacteria, or minerals, a bio-stimulant comprised of one or more of compounds, substances and micro-organisms for promoting crop vigor, improving crop yields and quality, and tolerance of abiotic stresses, and a plant growth regulator comprised of plant or soil inoculants that either increase or reduce a rate of metabolic processes in a plant;
    identifying one or more appropriate environmental predictors impacting biological processes in the particular field to develop an environmental profile for the performance of the soil-active agricultural biological product on the soil biota at a below-surface state represented in the below-ground spatial and temporal soil system attributes of the soil biota, and to analyze the below-surface state of the soil biota of the soil system in one or more machine learning models configured to construct variables describing the below-surface state and summarizing a correlated significance between above-ground weather data represented by weather and climatological information that includes at least one of recent and current field-level weather data, historical field-level weather data and extended-range weather forecast data for the specific geographical area and the below-ground spatial and temporal soil system attributes of the soil biota, and to match the variables summarizing a correlated significance with the one or more prior applications of the soil-active agricultural biological product;
    predicting a performance of soil-active agricultural biological product on the soil biota based on the environmental profile; and
    developing the targeted application schedule from the predicted below-ground performance for an application of a specific soil-active agricultural biological product at desired time or at a desired geographical location, wherein a user applies the specific soil-active agricultural biological product based on the targeted application schedule at the desired time or at the desired geographical location, or an automated application of the specific soil-active agricultural biological product at the desired time or at the desired geographical location is controlled based on the targeted application schedule.

13. The method of claim 12, further comprising applying the environmental profile to provide one or more advisories regarding an application of the soil-active agricultural biological product in any field at any selected time based on the prediction of the performance of the soil-active agricultural biological product.

14. The method of claim 12, further comprising analyzing a plurality of input data relative to the soil system, the particular field, and the soil-active agricultural biological product, the input data including soil-water information for the particular field, the soil-water information including one or more of surface and sub-surface drainage characteristics, an amount of water applied to the soil system through effective rainfall and irrigation, an amount of water that is retained in a dynamically-growing root zone, an amount of water depleted from the dynamically-growing root zone, and irrigation-specific information relative to past or recent irrigation activity.

15. The method of claim 14, wherein the input data further includes field-specific data that includes positional information identifying the particular field, the positional information including GPS data that enables usage of OPS receivers to determine one or more of positional coordinates and boundaries of the particular field.

16. The method of claim 14, wherein in the input data further includes soil-specific information for the particular field, the soil-specific information including one or more of a soil type, and known soil temperature and moisture content for at least one of a current growing season and a period of time extending up to and including a current growing season.

17. The method of claim 14, wherein in the input data further includes crop-specific information for the particular field, the crop-specific information including one or more of crop type data, planting data, crop growth data, growth stage-dependent parameters indicative of one or more crop growth stages, crop relative maturity data, crop planting depth and row spacing data, and targeted crop moisture or temperature thresholds.

18. The method of claim 14, wherein the input data further includes field-level remotely-sensed imagery data of the particular field.

19. The method of claim 12, further comprising developing one or more geographically-dispersed machine learning base models for a particular soil-active agricultural biological product, and applying the one or more geographically-dispersed machine learning base models to environmentally match the particular soil-active agricultural biological product for a particular geographic area.

20. The method of claim 19, further comprising training the one or more geographically-dispersed machine learning base models with performance data representing efficacy of the particular soil-active biological catalyst for a smaller local region to re-learn the one or more geographically-dispersed machine learning base models far a specific localized geographical area within the smaller local region.

21. The method of claim 12, further comprising building a comprehensive dataset for the customized field model of one or more physical and empirical characteristics impacting the soil biota of the soil system to automatically develop an artificial intelligence model to analyze time-varying characteristics of the soil biota of the soil system, and applying the artificial intelligence model to predict a below-ground performance of a soil-active agricultural biological product in any field at any selected time.

22. The method of claim 12, wherein the customized field model is further configured to determine an application of the soil-active agricultural biological product in conjunction with one or more of an additional biological product or a synthetic product in the particular field, and generate a prediction of the below-ground performance of the soil-active agricultural biological product and the one or more of an additional biological product or a synthetic product.

23. A system, comprising:
a computing environment including at least one computer-readable storage medium having program instructions stored therein and a computer processor operable to execute the program instructions to model a below-ground performance of a soil-active agricultural biological product within a plurality of data processing modules, the plurality of data processing modules including:

an initialization module configured to ingest above-ground weather data, represented by weather and climatological information that includes at least one of recent and current field-level weather data, historical field-level weather data and extended-range weather forecast data for a specific geographical area, crop-specific information relative to a crop in a particular field in the specific geographical area, soil-specific information relative to a soil system of the particular field, and a measured efficacy of the soil-active agricultural biological product in an outcome of one or more prior application of the soil-active agricultural biological product, wherein the soil-active agricultural biological product includes at least one of a biopesticide comprised of a biologically-derived pest control mechanism for plant, crop or soil protection, derived from organic materials such as one or more of animal matter, plant matter, bacteria, or minerals, a bio-stimulant comprised of one or more of compounds, substances and micro-organisms for promoting crop vigor, improving crop yields and quality, and tolerance of abiotic stresses, and a plant growth regulator comprised of plant or soil inoculants that either increase or reduce a rate of metabolic processes in a plant;

one or more modules configured to develop a customized field model of one or more physical and empirical characteristics impacting the below-ground performance of the soil-active agricultural biological product on soil biota of a soil system in a particular field, to enable a targeted application schedule at a desired time and a desired place to obtain a specific outcome, the customized field model configured to assess below-ground spatial and temporal attributes of importance to soil biota of the soil system that at least include soil moisture relative to a degree of soil pore saturation and soil temperature relative to a rate of physiological activity of soil biota at multiple depths and over multiple time periods, and characterize environmental factors influencing performance of the soil-active agricultural biological product on the soil biota of the soil system of the particular field, and develop an environmental profile for the performance of the soil-active agricultural biological product on the soil biota at a below-surface state represented in the below-ground spatial and temporal soil system attributes of the soil biota, by identifying one or more appropriate environmental predictors impacting biological processes in the particular field to analyze the below-surface state of the soil biota of the soil system in one or more machine learning models configured to construct variables describing the below-surface state of the soil biota and summarizing a correlated significance of above-ground weather data for a specific geographical area including the particular field and the below-ground spatial and temporal soil system attributes of the soil biota, and match the variables summarizing the correlated significance with the one or more prior applications of the soil-active agricultural biological product;

a prediction module configured to generate a prediction of the below-ground performance of the soil-active agricultural biological product on the soil biota from the environmental profile; and an output module configured to develop the targeted application schedule from the predicted below-ground performance for application of a specific soil-active agricultural biological product at desired time or at a desired geographical location, wherein a user applies the specific soil-active agricultural biological product based on the targeted application schedule at the desired time or at the desired geographical location, or an automated application of the specific soil-active agricultural biological product at the desired time or at the desired geographical location is controlled based on the targeted application schedule.

24. The system of claim 23, wherein the environmental profile is applied to provide one or more advisories regarding an application of the soil-active agricultural biological product in any field at any selected time based on the prediction of the performance of the soil-active agricultural biological product.

25. The system of claim 23, wherein the input data further includes field-specific data that includes positional information identifying the particular field, the positional information including GPS data that enables usage of GPS receivers to determine one or more of positional coordinates and boundaries of the particular field.

26. The system of claim 23, wherein the input data further includes soil-water information for the particular field, the soil-water information including one or more of surface and sub-surface drainage characteristics, an amount of water applied to the soil system through effective rainfall and irrigation, an amount of water that is retained in a dynamically-growing root zone, an amount of water depleted from the dynamically-growing root zone, and irrigation-specific information relative to past or recent irrigation activity for the particular field.

27. The system of claim 23, where the soil-specific information includes one or more of a soil type, and known soil temperature and moisture content for at least one of a current growing season and a period of time extending up to and including a current growing season.

28. The system of claim 23, wherein the crop-specific information further includes one or more of crop type data, planting data, crop growth data, growth stage-dependent parameters indicative of one or more crop growth stages, crop relative maturity data, crop planting depth and row spacing data, and targeted crop moisture or temperature thresholds.

29. The system of claim 23, wherein the input data further includes field-level remotely-sensed imagery data of the particular field.

30. The system of claim 23, wherein the one or more modules are further configured to develop one or more geographically-dispersed machine learning base models for a particular soil-active agricultural biological product, and apply the one or more geographically-dispersed machine learning base models to environmentally match the particular soil-active agricultural biological product for a particular geographic area.

31. The system of claim 30, wherein the one or more modules are further configured to train the one or more geographically-dispersed machine learning base models with performance data representing efficacy of the particular soil-active agricultural biological product for a smaller local region to re-learn the one or more geographically-dispersed machine learning base models for a specific localized geographical area within the smaller local region.

32. The system of claim 23, wherein the one or more modules are further configured to build a comprehensive dataset for the customized field model of one or more physical and empirical characteristics impacting the soil biota of the soil system to automatically develop an artificial intelligence model to analyze time-varying characteristics of the soil biota of the soil system, and applying the artificial intelligence model to predict a below-ground performance of a soil-active agricultural biological product in any field at any selected time.

33. The system of claim 23, wherein the customized field model is further configured to determine an application of the soil-active agricultural biological product in conjunction with one or more of an additional biological product or a synthetic product in the particular field, and generate a prediction of the below-ground performance of the soil-active agricultural biological product and the one or more of an additional biological product or a synthetic product.

* * * * *